United States Patent [19]

Davis

[11] Patent Number: 4,854,316

[45] Date of Patent: Aug. 8, 1989

[54] APPARATUS AND METHOD FOR REPAIRING AND PREVENTING PARA-STOMAL HERNIAS

[76] Inventor: Emsley A. Davis, 1616 Colcord Ave., Waco, Tex. 76707

[21] Appl. No.: 915,041

[22] Filed: Oct. 3, 1986

[51] Int. Cl.⁴ .............. A61B 17/04; A61F 1/00; A61F 2/12

[52] U.S. Cl. .................... 128/334 R; 623/12; 623/66; 128/898; 604/8; 604/337; 604/175

[58] Field of Search ............ 128/1 R, 334 R, 334 C; 623/11, 12, 14, 66; 604/8, 29, 329, 175

[56] References Cited

U.S. PATENT DOCUMENTS

| | | | |
|---|---|---|---|
| 3,540,451 | 11/1970 | Zeman | 604/8 |
| 3,633,585 | 1/1972 | McDonald | 604/8 |
| 3,783,868 | 1/1974 | Bokros | 623/66 |
| 3,818,511 | 6/1974 | Goldberg et al. | 128/334 R |
| 3,881,199 | 5/1975 | Treace | 623/12 |
| 4,121,589 | 10/1978 | McDonnell | 604/328 |
| 4,217,664 | 8/1980 | Faso | 623/11 |
| 4,347,847 | 9/1982 | Usher | 128/334 R |

FOREIGN PATENT DOCUMENTS 0923553 5/1982 U.S.S.R. .......... 128/334 R

OTHER PUBLICATIONS

Redo et al, "Gastrostomy with a Prosthesis." Sargery, vol. 61, No. 2, pp. 320-324.
Chaimoff C; Bayer I, "New Procedure for Preventing Paracolostomy Hernia and Prolapse." Israel Journal of Medical Sciences, vol. 20, 1984, pp. 1207-1208.
Sugarbaker, P. H., "Prosthetic Mesh Repair of Large Hernias at the Site of Colonic Stomas." Surg. Gynecol. Obstet. Apr. 1980 150 (9) pp. 576-578.
Bayer, I., Kyzer, S., and Chaimoff, Ch., "A New Approach to Primary Strengthening of Colostomy with Marlex Mesh to Prevent Paracolostomy Hernia". Surg. Gynecol. Obstet., Dec. 1986, 163 (6) pp. 579-580.
Abdu, Rashid A., "Repair of Paracolostomy Hernias with Marlex Mesh". Dis Colon Rectum. Sep. 1982, 25 (6) pp. 529-531.

Primary Examiner—Edward M. Coven
Assistant Examiner—Gary Jackson
Attorney, Agent, or Firm—Arthur F. Zobal; James C. Fails; Geoffrey A. Mantooth

[57] ABSTRACT

A sheet-like inner member formed of prosthetic mesh has an opening formed therethrough. A tubular member formed of prosthetic mesh has two opposite ends with an opening extending therethrough between its two ends. The inner member is connected to the tubular member at or near one end thereof such that a passage extends through the openings of the two members. The tubular member is adapted to be located in the opening of an abdominal wall of a human inward of the outer skin thereof with the inner member being adapted to be attached to an inner portion of the abdominal wall around the opening thereof inward of the other end of the tubular member. The passage of the device has a size sufficient to receive and support a portion of the gastro-intestinal tract. In another embodiment a sheet-like outer member formed of prosthetic mesh and having an opening formed therethrough is connected to the tubular member at or near its other end such that the passage of the device extends through the opening of the outer member. The outer member is adapted to be attached to an outer portion of the abdominal wall around the opening thereof inward of the outer skin. For use in repairing a stomal hernia, the device has a slit or a gap formed through one side thereof whereby it may be located around the gastrointestinal tract and sutured in place without disturbing the stomal bud.

7 Claims, 3 Drawing Sheets

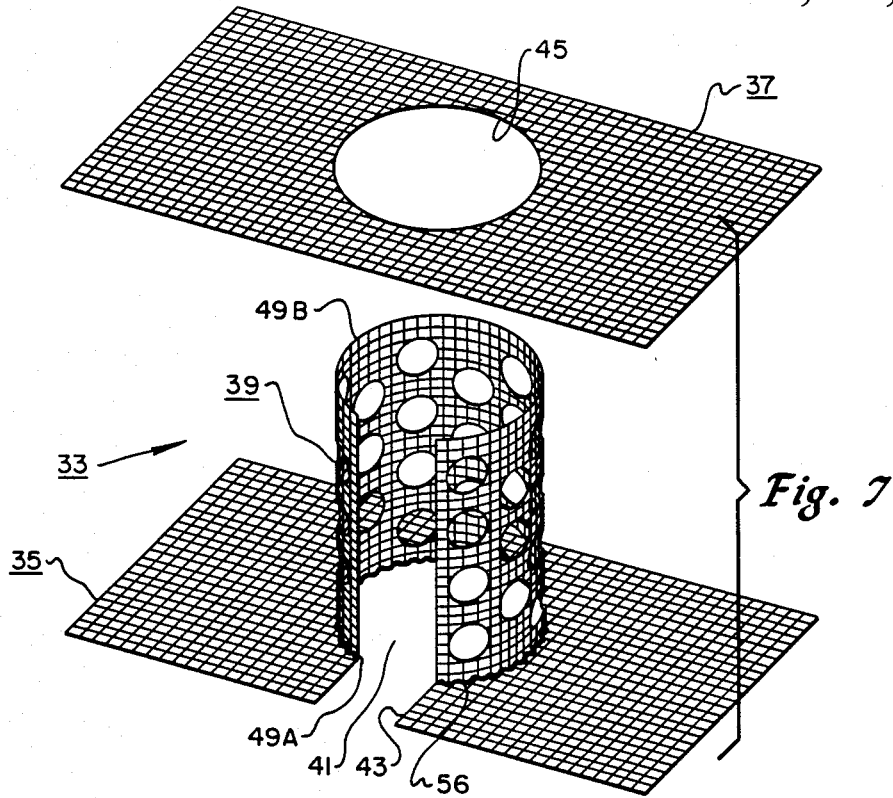
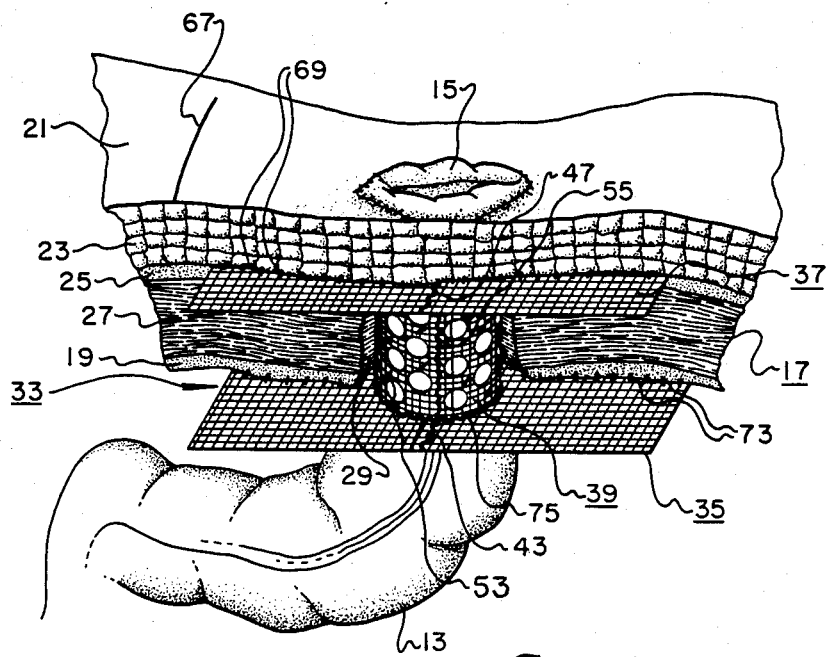

APPARATUS AND METHOD FOR REPAIRING AND PREVENTING PARA-STOMAL HERNIAS

FIELD OF THE INVENTION

The invention relates to a device for use in conjunction with stomas resulting from colostomies, ileostomies, and gastrostomies.

BACKGROUND OF THE INVENTION

In a colostomy, a human patient's colon is rerouted from the non-functioning anus to a stoma located in the patient's abdominal region. In performing the operation, an opening is made in the abdominal wall of the patient to receive the lowermost end portion of the colon. The lower-most end of the colon is then sutured to the skin around the perimeter of the abdominal wall opening. After a colostomy, a common occurrence is for the colon, and occasionally the small intestine, to move through portions of the abdominal wall opening, causing the outer portions of the abdominal wall to bulge outwardly in the region around the stoma. Such a bulge is known as a para-stomal hernia, or more specifically, as a para-colostomy hernia. The same type of bulging can occur when the small intestine has been routed to the stoma, thus forming a para-ileostomy hernia. A para-stomal hernia is troublesome to the patient in that it causes physical discomfort and unsightliness. In addition, a para-colostomy or a para-ileostomy hernia may make it more difficult for the patient to evacuate and may cause dislodgement of evacuation appliances.

A prior art device which is directed to the problem of a para-colostomy hernia consists of a circular piece of prosthetic mesh which is sutured to the inner side of the abdominal wall such that the abdominal wall opening is centrally located relative to the mesh. The colon is led out over the mesh and secured to the abdominal wall, while that portion of the colon nearest the stoma is interposed between the mesh and the outer portion of the abdominal wall. The prior art device does not, however, satisfactorily prevent the colon from moving through the abdominal wall opening and thus does not prevent herniation.

SUMMARY OF THE INVENTION

It is an object of the invention to provide a device and technique for repairing and preventing para-stomal hernias in humans.

The device comprises a sheet-like member having an opening formed therethrough and a tubular member having two opposite ends with an opening extending therethrough between its two ends. The sheet-like member is connected to the tubular member at or near one end thereof such that a passage extends through the openings of the two members.

The tubular member is adapted to be located in the opening of the abdominal wall inward of the outer skin thereof with the sheet-like member being adapted to be attached to an inner portion of the abdominal wall around the opening thereof inward of the other end of the tubular member. The passage of the device has a size sufficient to receive and support a portion of the gastrointestinal tract when the tubular member is located in the opening of the abdominal wall inward of the outer skin and when the sheet-like member is attached to an inner portion of the abdominal wall around the opening thereof inward of the other end of the tubular member.

The sheet-like member and tubular member are formed of a material that is flexible; suitable for surgical application; suturable to abdominal wall tissue; and acceptable to a human biological system.

In another embodiment the device comprises a second sheet-like member having an opening formed therethrough. The second sheet-like member is formed of the same material as that of the first sheet-like member and tubular member. The second sheet-like member is connected to the tubular member at or near its other end such that the passage of the device extends through the opening of the second sheet-like member. The second sheet-like member is adapted to be attached to an outer portion of the abdominal wall around the opening thereof, inward of the outer skin, preferably to the fascia.

In a preferred embodiment each of the three members of the device is formed of prosthetic mesh.

For use in repairing a stomal hernia, the device has a slit or gap formed through one side thereof whereby it may be located around the gastrointestinal tract and sutured in place without disturbing the stomal bud.

BRIEF DESCRIPTION OF THE DRAWINGS

FIG. 7 is a schematic isometric view of the device of the invention in a partially assembled state for simplifying insertion.

FIG. 8 is a schematic partial cut away view showing the device installed in a patient.

DESCRIPTION OF THE PREFERRED EMBODIMENTS

Figure 1:
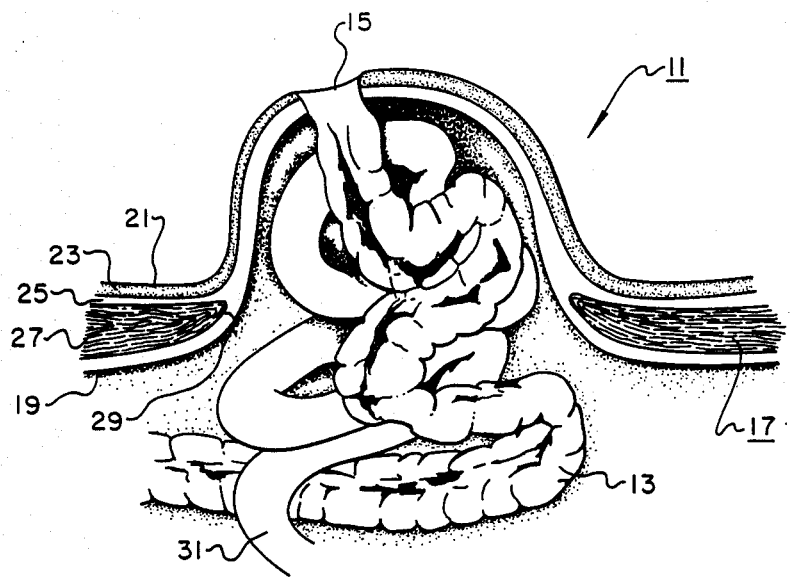
FIG. 1 is a cross-sectional view of a para-colostomy hernia.

In FIG. 1 there is shown a cross-sectional view of a typical para-colostomy hernia 11 as occurring in a human patient. The patient has undergone a colostomy wherein his colon 13 has been rerouted away from the non-functioning anus to a stoma 15 in the abdominal wall 17. The abdominal wall comprises the peritoneum 19 on the inside and skin 21 on the outside. Between these layers are the subcutaneous tissue 23, the fascia 25, and muscle tissue 27. In performing the colostomy, an opening is made in the abdominal wall 17 for receiving the colon 13. Although the skin 21 and peritoneum 19 close up around the colon 13, the fascia 25 and the muscle tissue 27 do not, thereby leaving an opening 29 through these layers in the abdominal wall. Herniation occurs when the colon 13, either alone or together with the small intestine 31, moves through the opening 29 and causes a bulging in the skin 21 and peritoneum 19.

Figure 2:
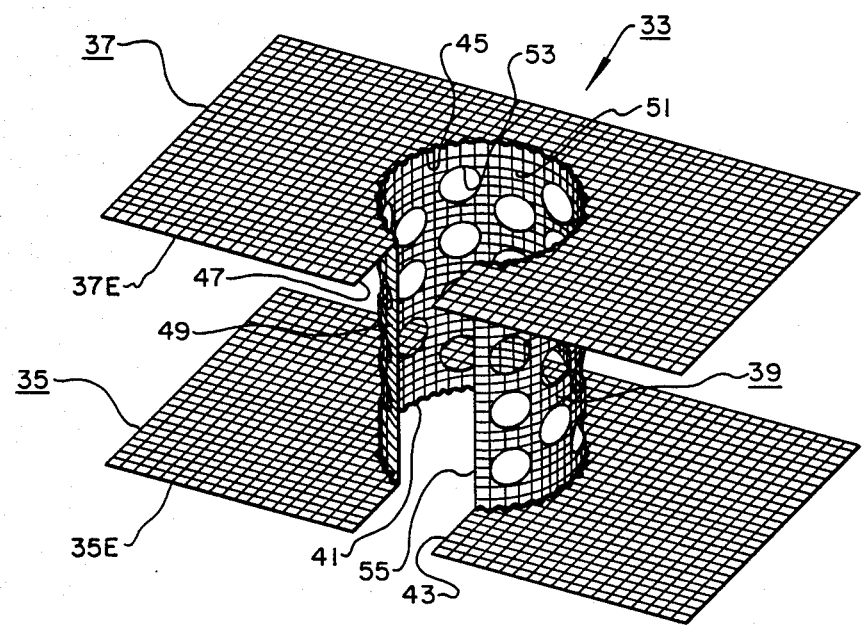
FIG. 2 is a schematic isometric view of the device of the invention, in accordance with a preferred embodiment.

The device or apparatus 33 of the invention, in accordance with one embodiment, for use for repairing and preventing a para-colostomy hernia will now be described, with particular reference to FIG. 2. The device 33 comprises an inner member 35, an outer member 37 and a tubular member 39.

The inner member 35 is a single sheet of material having a centrally located circular opening 41. The opening 41 is of a size sufficient to allow location of the colon 13 therein. The remainder of the inner member 35, surrounding the opening, is of sufficient size to allow itself to be attached to that portion of the abdominal wall 17 around the opening 29. A gap 43 or slit extends from the opening 41 of member 35 to its perimeter. The purpose of the gap will be explained hereinafter. The outer member 37, which is substantially similar to the inner member 35, also has an opening 45 and a gap 47. Although the members 35 and 37 are shown in FIG. 2 as having rectangular shapes, they may have other shapes.

The tubular member 39 is generally cylindrical in shape and comprises a wall 49 having an inner end 49A and an outer end 49B. The length of the member 39 between its ends 49A and 49B is approximately equal to the distance traversed between the underside of the peritoneum and the under surface of the skin including muscle, subcutaneous tissue, and the facia. The member 39 has a cylindrical cavity or opening 51 that extends between its two ends 49A and 49B. The cavity 51 is of a sufficient transverse dimension to receive and contain therein a portion of the length of the colon. The wall 49 has a gap 55 that extends along the length of the member 39 between its ends 49A and 49B. Although the tubular member 39 is shown in FIG. 2 as having a generally cylindrical shape, the member may have other shapes.

Each of the members 35, 37 and 39 is made of a material that is suitable for surgical application. The material should be relatively flexible to allow for both patient comfort and ease in installation. The material should also be suturable to the abdominal wall tissue and acceptable to the patient's biological systems so that the material will not be rejected. A suitable material that has been found to be satisfactory is prosthetic mesh such as is commercially available under the name "Marlex". Marlex prosthetic mesh is available in sheets of varying dimensions and is made of woven 6 mil monofilament knitted polypropylene. Each of the openings of the mesh has dimensions of about 6 mils by 6 mils. Prosthetic mesh allows the tissue to grow into the holes between the monofilaments and becomes incorporated into the surrounding tissue.

Figure 3:
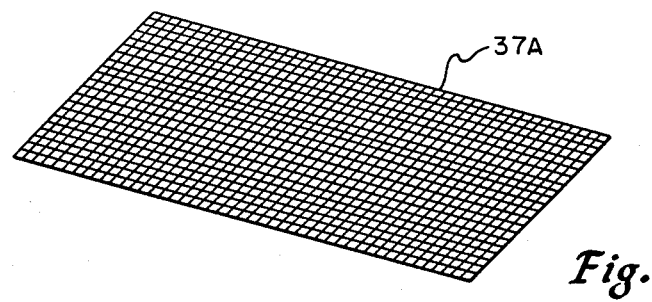
FIGS. 3–5 are schematic isometric views of three sheets of prosthetic mesh before fabrication into the device of FIG. 2.
Figure 4:
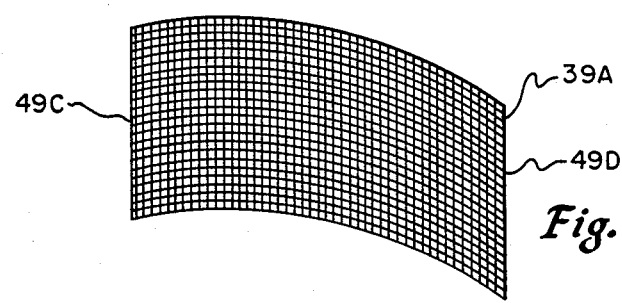
Figure 5:
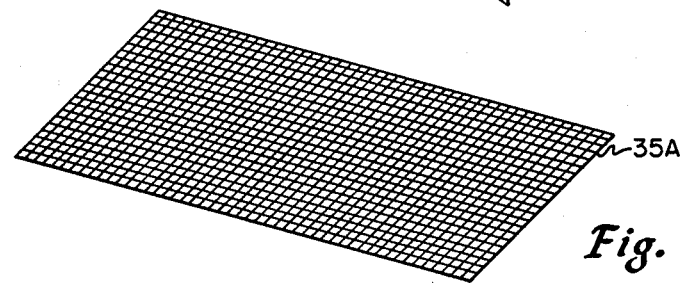

In the preferred embodiment, the device 33 is assembled from three sheets or leaves 35A, 37A and 39A of prosthetic mesh, as shown in FIGS. 3, 4 and 5. Each of the sheets 35A and 37A may be originally square, with each side having a dimension of 15 centimeters. They are cut to the desired size and shape to form the members 35 and 37 each of which will be larger than the abdominal wall opening 29, thereby enabling the attachment of the members 35 and 37 to the appropriate layers of the abdominal wall around the opening 29. A circular portion of mesh having a diameter corresponding to the diameter of the colon is removed from the center of each of the sheets 35A and 37A to form the openings 41 and 45 of the members 35 and 37. The sheet 39A of prosthetic mesh from which the tubular member 39 is formed has a width that is approximately the same as the circumference of the colon 13. The sheet from which the member is formed may be perforated with a sterile paper punch to form perforations 53 to enhance the flexibility of the prosthetic mesh and to facilitate tissue growth into the prosthetic mesh. The sheet is then bent into a cylinder with its side edges 49C and 49D brought together and the ends 49A and 49B of the member 39 are sutured at 56 to the edges of the members 35 and 37 surrounding their openings 41, 45 (see FIG. 4). The seam 55 of the tubular member 39 between its side edge 49C and 49D is unsutured. The cavity 51 within the member 39 is of the same transverse dimension as that of the openings 41 and 45 of the members 35 and 37 and the cavity 51 at the ends 49A and 49B of the member 39 is aligned with the openings 41 and 45 of members 35 and 37. A passage thus extends through the openings 41, 51, and 45 of the members 35, 39, and 37 of the device 33. The tubular member 39, with its side edges 49C and 49D brought together, has dimensions such that it will fit without constriction around the colon segment from the peritoneum up to the facia of the external oblique muscle. For use for repair purposes, the device 33 is split along one side through the seam 55 by cutting slits in members 35 and 37 from their edges 35E and 37E inward to their openings 41 and 45 with the slits being aligned with the seam 55 to form the gaps 43, 47 in the members 35 and 37 (see FIG. 2). In this manner, the gaps 43, 47 and 49 of members 35, 37 and 39 are aligned.

Referring to FIG. 8, the installation of the device 33 into a human patient, for the repair of a para-colostomy hernia, without disturbing the stomal bud will now be described. The bowel is prepared with enemas and antibiotics, including a short course of perioperative systematic antibiotics. An adhesive drape is used to exclude the colostomy stoma from the operative field, and the abdominal cavity entered and explored, preferably through the original incision 67 that was made when the colostomy was established. Next, the colonic segment is freed by both sharp and blunt dissection in its full circumference from the peritoneum externalward to the aponeurosis of the external oblique muscle. The fascial layer 25 is sharply dissected from the subcutaneous tissue 23 five to six centimeters in all directions around the colon. This maneuver may be accomplished more easily from the edge of the main wound laterally rather than centrifugally from the colon. The hernia sac having been removed and the fascial defect repaired with non-absorbable sutures, the redundant colon is reduced intra-abdominally.

The device 33 is spread apart at its gaps, inserted through the incision, and passed around the colon to locate a segment of the colon within the cavity 51 and openings 41 and 45, with the member 37 located between subcutaneous tissue 23 and the facia 25. The member 37 is sutured at 69 to both layers 23 and 25, closing its gap 47. The member 35 is sutured at 73 to the underside of the peritoneum closing its gap 43. If desired, the edges of the member 37 forming the gap 47 may be sutured together; the edges of the member 35 forming the gap 43 be sutured together; and the edges 49C and 49D of the tubular member 39 may be sutured together. The colon is now sutured at 75 to the device 33 at the junction between members 35 and 39. The colon also may be sutured to the device 33 at the junction between members 37 and 39. In addition, if desired, the colon may be sutured to the tubular member 39 along its length. Routine precaution is taken against internal herniation, after which irrigation of the peritoneal cavity and closure of the abdominal wall is performed.

Thus the device 33 supports all tissues around the colon on three surfaces and its use may be defined as a triperimetrical prosthetic mesh repair. When installed, the colon is supported and confined by the tubular member 39 which restricts any lateral swelling or bulging and hernia inducing movement of the colon near the stoma.

FIG. 7 illustrates the device 33 partially pre-formed in two pieces to save some anesthesia time. The tubular member 39 has its end 49A sutured at 56 to the inner member 35. The outer member 37 is unattached to the end 49B of the tubular member 39. Having the end 49B of member 39 unattached allows the surgeon to cut the member 39 to the desired length which will vary from person to person depending on the abdominal wall thickness. The surgeon can easily form a gap in the gapless outer member 37 of FIG. 7 and suture the member 37 to the end 49B of the tubular member 39 prior to insertion and attachment of the device 33 in place as described above.

Figure 6:
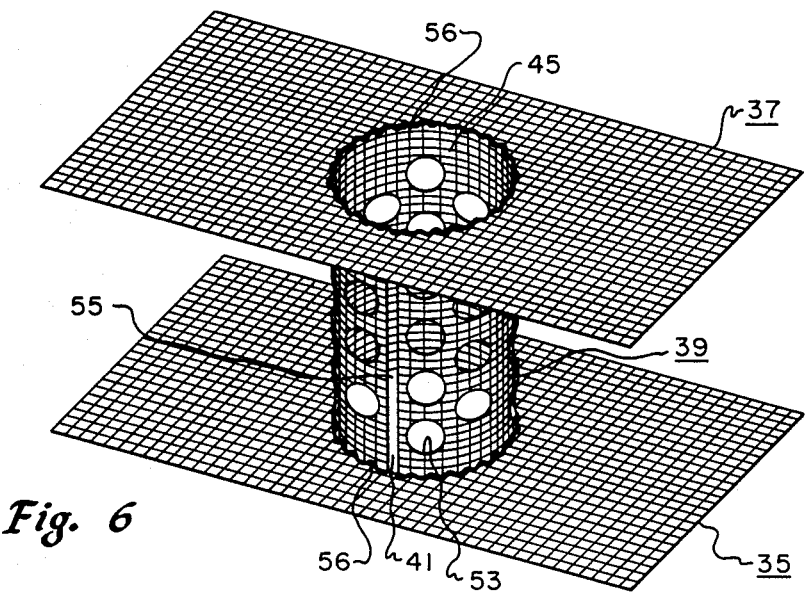
FIG. 6 is a schematic isometric view of the device of the invention, showing the inner member and the outer member without gaps.

Since the device 33 supports all the pericolic tissue, its use is recommended at the initial establishment of a new colostomy. In a new colostomy the gaps 43, 47 and 55 of the members 35, 37 and 39 are not necessary whereby the device as shown in FIG. 6 may be employed. The colon will be inserted through the openings 41, 51, and 45 of members 35, 39, and 37 and the device 33 sutured in place to the peritoneum and external oblique fascia and to the colon as described previously. At the option of the surgeon, in a new colostomy, the upper layer 37 of the device 33 may not be employed. In this embodiment, the upper end 49B of the tubular member 39 may be sutured to the external oblique facia 25. In new cases suturing of the device to the oblique fascia may be optional.

Although the device and process of the invention were described as being used for the repair of paracolostomy hernias at the stomal site and for preventing such hernias in a newly constructed colostomy, it could also be used for the same purposes in ileostomies and gastrostomies. In an ileostomy, a portion of the small bowel or ileum will extend through and be supported by the device 33 and in a gastrostomy, a portion of the stomach will extend through and be supported by the device 33. Thus the device of the invention can be used to support the colon, ileum, or stomach of the gastrointestinal tract to repair or prevent hernias at the stomal site in a colostomy, ileostomy, or gastrostomy.

Although the members 35 and 37 are shown as being attached flush with the ends 49A and 49B of the tubular member 39, it is to be understood that the members 35 and 37 may be attached to the member 39 near but inward of its ends 49A and 49B if desired.

I claim:

1. A device for use in repairing and preventing a para-stomal hernia in a human, the stoma resulting from the rerouting of a portion of the gastrointestinal tract of the human through an opening in the abdominal wall, said device comprising:

a sheet-like inner member having an opening formed therethrough, a tubular member having two opposite ends with an opening extending therethrough between said two ends, said inner member being connected to said tubular member at or near one end thereof such that a passage extends through said openings of said inner member and of said tubular member, said tubular member being adapted to be located in the opening of the abdominal wall inward of the outer skin of the abdominal wall with said inner member being adapted to be attached to an inner portion of the abdominal wall near the opening thereof inward of the other end of said tubular member, said passage of said device having a size sufficient to receive and support a portion of the gastrointestinal tract located in the opening of the abdominal wall inward of the outer skin and when said inner member is attached to an inner portion of the abdominal wall near the opening thereof inward of the other end of said tubular member, a sheet-like outer member having an opening formed therethrough, said outer member being connected to said tubular member at or near its other end such that said passage extends through said opening of said outer member, said outer member being adapted to be attached to an outer portion of the abdominal wall near the opening thereof inward of the outer skin, said inner member, said tubular member, and said outer member being formed of prothetic mesh comprising a material that is relatively flexible; is suitable for surgical application; is suturable to abdominal wall tissue; and is acceptable to a human biological system.

2. The device of claim 1, wherein:

said inner member has a gap extending between its outer edge and its opening, said outer member has a gap extending between its outer edge and its opening, the wall of said tubular member has a gap extending between its two opposite ends, said inner and outer members being connected to said tubular member such that their gaps are aligned to allow said device to be located around the gastrointestinal tract with a portion of the gastrointestinal tract located within said passage of said device whereby said device may be employed for repairing a para-stomal hernia without disturbing the stomal bud.

3. The device of claim 2, wherein:

said tubular member has two edges defining said gap of said tubular member, when said two edges of said tubular member are located next to each other, the wall of said tubular member between said two ends thereof, when viewed from either of said two ends, is continuous between said two edges for substantially 360°.

4. A method of repairing and preventing a para-stomal hernia in a human, the stoma resulting from the rerouting of a portion of the gastrointestinal tract of the human through an opening in the abdominal wall, said method comprising the steps of:

entering the human through an incision in the abdominal wall to gain access to the gastrointestinal tract located in the abdominal cavity, locating a section of the gastrointestinal tract within the passage of a device comprising a sheet-like inner member having an opening formed therethrough, a tubular member having two opposite ends with an opening extending therethrough between said two ends and a sheet-like outer member having an opening formed therethrough with said inner member being connected to said tubular member at or near one ned thereof and said outer member being connected to said tubular member at or near the other end thereof such that said passage extends through said openings of said inner member, of said outer member, and of said tubular member, with most of the length of said passage extending through said opening of said tubular member, said device having a gap formed through one side thereof such that said device is spread apart at its gap to locate the gastrointestinal tract within said passage of said device without disturbing the stomal bud, said inner member, said tubular member, and said outer member being formed of a prosthetic mesh comprising a material that is relatively flexible; is suitable for surgical application; is suturable to abdominal wall tissue; and is acceptable to a human biological system, with said section of the gastrointestinal tract located within said passage of said device, and with said tubular member being located in the opening of the abdominal wall inward of the outer skin thereof, attaching said outer member to an outer position of the abdominal wall around near the opening thereof inward of the outer skin of the abdominal wall and said inner member to an inner portion of the abdominal wall around near the opening thereof inward of said outer member, when said section of the gastrointestinal tract is located within said passage of said device and said outer member is attached to said outer portion of the abdominal wall and said inner member is attached to said inner portion of the abdominal wall, said tubular member between said two ends thereof, extends substantially continuously around said section of the gastrointestinal tract providing, between said two ends thereof, substantially continuous support and confinement for said section of the gastrointestinal tract around the periphery thereof.

5. A device for use in repairing and preventing a para-stomal hernia in a human, the stoma resulting from the rerouting of a portion of the gastrointestinal tract of the human through an opening in the abdominal wall, said device comprising:

a sheet-like member having an opening formed therethrough, a tubular member having two opposite ends with an opening extending therethrough between said two ends, said sheet-like member being connected to said tubular member at or near one end thereof such that a passage extends through said openings of said sheet-like member and of said tubular member, said tubular member being adapted to be located in the opening of the abdominal wall inward of the outer skin of the abdominal wall with said sheet-like member being adapted to be attached to a portion of the abdominal wall near the opening thereof inward of the outer skin of the abdominal wall, said passage of said device having a size sufficient to receive and support a portion of the gastrointestinal tract of a human when said tubular member is located in the opening of the abdominal wall inward of the outer skin and when said inner member is attached to a portion of the abdominal wall near the opening thereof inward of the outer skin, a second sheet-like outer member having an opening formed therethrough, said second sheet-like member having connected to said tubular member at or near its other end such that said pressure extends through said opening of said sheet-like member, said second sheet-like member being adapted to be attached to a portion of the abdominal wall near the opening thereof inward of the outer skin, said sheet-like member, said tubular member, and said second sheet-like member being formed of a prosthetic mesh comprising a material that is relatively flexible; is suitable for surgical application; is suturable to abdominal wall tissue; and is acceptable to a human biological system.

6. The device of claim 5, wherein:

the wall of said tubular member between said two ends thereof, when viewed from either of said two ends, is continuous for substantially 360°.

7. A device for use in repairing and preventing a para-stomal hernia in a human, the stoma resulting from the rerouting of a portion of the gastrointestinal tract of the human through an opening in the abdominal wall, said device comprising:

a sheet-like inner member having an opening formed therethrough, a tubular member having two opposite ends with an opening extending therethrough between said two ends, said inner member being connected to said tubular member at or near one end thereof such that a passage extends through said openings of said inner member and of said tubular member, said tubular member being adapted to be located in the opening of the abdominal wall inward of the outer skin of the abdominal wall with said inner member being adapted to be attached to an inner portion of the abdominal wall near the opening thereof inward of the other end of said tubular member, said passage of said device having a size sufficient to receive and support a portion of the gastrointestinal tract of a human when said tubular member is located in the opening of the abdominal wall inward of the outer skin and when said inner member is attached to an inner portion of the abdominal wall near the opening thereof inward of the other end of said tubular member, a sheet-like outer member having an opening formed therethrough, said outer member being connected to said tubular member at or near its other end such that said passage extends through said opening of said outer member, said outer member being adapted to be attached to an outer portion of the abdominal wall near the opening thereof inward of the outer skin, said inner member has a gap extending between its outer edge and its opening, said outer member has a gap extending between its outer edge and its opening, the wall of said tubular member has a gap extending its two opposite ends, said inner and outer members being connected to said tubular member such that their gaps are aligned to allow said device to be located around the gastrointestinal tract located within said passage of said device whereby said device may be employed for repairing a para-stomal hernia without disturbing the stoaml bud, said inner member, said tubular member, and said outer member being formed of a material that is relatively flexible; is suitable for surgical application; is suturable to abdominal wall tissue; and is acceptable to a human biological system.

* * * * *